United States Patent
Gush et al.

(10) Patent No.: US 11,950,894 B2
(45) Date of Patent: Apr. 9, 2024

(54) OPTICAL COHERENCE IMAGER

(71) Applicant: Moore Instruments Limited, Axminster (GB)

(72) Inventors: Rodney John Gush, Axminster (GB); Xiabing Huang, Axminster (GB)

(73) Assignee: Moore Instruments Limited, Axminster (GB)

( * ) Notice: Subject to any disclaimer, the term of this patent is extended or adjusted under 35 U.S.C. 154(b) by 700 days.

(21) Appl. No.: 16/972,462

(22) PCT Filed: Jun. 5, 2019

(86) PCT No.: PCT/GB2019/051564
§ 371 (c)(1),
(2) Date: Dec. 4, 2020

(87) PCT Pub. No.: WO2019/234428
PCT Pub. Date: Dec. 12, 2019

(65) Prior Publication Data
US 2021/0161407 A1  Jun. 3, 2021

(30) Foreign Application Priority Data
Jun. 5, 2018 (GB) .................................. 1809229

(51) Int. Cl.
*A61B 5/026* (2006.01)
*A61B 5/00* (2006.01)
(52) U.S. Cl.
CPC .......... *A61B 5/0261* (2013.01); *A61B 5/7257* (2013.01); *A61B 5/742* (2013.01)
(58) Field of Classification Search
CPC ...... A61B 5/0261; A61B 5/7257; A61B 5/742
See application file for complete search history.

(56) References Cited

U.S. PATENT DOCUMENTS 6,173,197 B1   9/2001  Boggett et al.
10,448,850 B2 * 10/2019 Wang .................. A61B 5/0295
(Continued)

OTHER PUBLICATIONS

Sanne et al. ; "Applicability of quantitative optical imaging techniques for intraoperative perfusion diagnostics: a comparison of laser speckle contrast imaging, sidestream dark-field microscopy, and optical coherence tomography"; Journal of Biomedical Optics; vol. 22 (8) 086004. pp 1-9 (Year: 2017).*

(Continued)

*Primary Examiner* — Dixomara Vargas
(74) *Attorney, Agent, or Firm* — Sandberg Phoenix & von Gontard PC

(57) ABSTRACT

An optical coherence imager for use in a clinical environment includes a laser source (24) for illuminating an area of tissue surface and a detector array (28) arranged to generate output signals indicative of detected light scattered from the tissue surface. An optical coherence image, such as a Flux image that is indicative of blood perfusion in the tissue, is generated from data collected at the detector. Detector output is analysed to identify a time series of such optical coherence images during which relative movement between tissue and detector is favourable. A representative optical coherence image is formed from an average of optical coherence images generated from data collected within the identified time series and extending over a period of multiple heartbeats. The representative optical coherence image thereby exhibits minimal movement noise and the effects of heartbeat are averaged out.

29 Claims, 11 Drawing Sheets

(56) References Cited

U.S. PATENT DOCUMENTS

2012/0277559 A1* 11/2012 Kohl-Bareis ........ A61B 5/0261
600/479
2016/0345820 A1* 12/2016 Frisken ................ A61B 3/0025

OTHER PUBLICATIONS

International Search Report for PCT/GB2019/051564 dated Feb. 8, 2019.
Written Opinion for PCT/GB2019/051564 dated Feb. 8, 2019.
Yali Jia et al.: "Split-Spectrum Amplitude-Decorrelation Angiography with Optical Coherence Tomography", (Feb. 13, 2012), vol. 20, No. 4, Optics Express 4710.
Becher, H. et al.: Handbook of Contrast Echocardiology Left ventricular function and myocardial perfusion (Jun. 1, 2000), pp. 1-72.

* cited by examiner

OPTICAL COHERENCE IMAGER

CROSS-REFERENCE TO RELATED APPLICATIONS

This application is a National Stage of International Application No. PCT/GB2019/051564, filed on Jun. 5, 2019 (Publication No. WO 2019/234428), which claims priority to GB Patent No. 1809229.6, filed on Jun. 5, 2018, the disclosures of the which are incorporated herein by reference.

This invention relates to the field of optical coherence imaging. Optical coherence imagers generate an image that is derived from interference effects observed when coherent light interacts with matter. In particular, this invention relates to a method and apparatus for identifying a period of stability during image acquisition that enables generation of an image with reduced sensitivity to subject movement. This invention should find particular application to coherence imaging of blood flow in a surgical environment. In this environment, unintentional tissue movement degrades image quality. In addition, physiological factors such as heartbeat cause fluctuations in tissue perfusion, which can obscure meaningful data. An exemplary application is to reconstructive plastic surgery and, in particular, to a method and apparatus to assist with the assessment of body tissue to determine its viability for use in such surgery.

Autologous reconstruction uses tissues from another part of a patient's body to reconstruct a damaged or missing part. It is a widely used technique in breast reconstruction in which tissue (skin, fat and sometimes muscle), usually from the back, abdomen or buttocks, is reshaped and stitched to its new position. The "flap", as it is termed, can be completely separated from its original blood vessels and moved to the chest (free flap reconstruction) or it can remain attached and moved beneath the patient's skin (pedicled flap reconstruction).

In all cases, it is important to ensure that the flap tissue receives an adequate blood supply. Venous congestion or arterial thrombosis of the anastomosis are relatively rare events that can result in total flap failure. Such single vessel blockages are generally identifiable by ultrasound. More common post-operative complications arise through tissue necrosis. This is due to inadequate blood flow within the body tissue in small terminal vessels, which are easily constricted or blocked through the trauma of operation. Blockages are not readily apparent in such small vessels. One of the fundamental causes of early complications following a reconstructive procedure is thought to be inadequate tissue perfusion.

Many studies, with widely varying results, have been carried out on post-operative complications in breast reconstruction. One study found rates of fat necrosis in autologous tissue reconstruction to be 46% in Caucasians, rising to 78% in African Americans. Another study, which focused on patient-reported outcomes, put the complication rate at 35%. For non-autologous, implant breast reconstruction, a recent study described a 13.8% complication rate. Surgeons perform more than 80,000 breast reconstructions in the USA and 6,000 in the UK each year. Based on these, and other, findings, it is clear that the complication rate means increased stress and discomfort for a significant number of patients. The burden on the medical profession is increased, with complications leading, at best, to more post-recovery visits and often to further operations.

Imaging techniques have been developed to enable surgeons to assess tissue viability during an operation. This enables the immediate implementation of procedures to avoid post-operative complications. For example, tissue areas of poor viability potential can be discarded and tissue with adequate blood perfusion used instead. Alternatively, venous drainage from the tissue area can be improved. Several perfusion imaging techniques have been used in free flap reconstructions, the most common in current use being indocyanine green (ICG) fluorescence. The ICG dye is injected via a patient's vein into the blood stream and so will be carried by blood flow into tissue. Illumination of the site of interest with a suitable light source renders the fluorescent dye visible in an image taken through the skin. The degree of blood perfusion into the tissue will be indicated by the distribution and intensity of the fluorescence. Despite the fact that fluorescence intensity varies with time and with patient physique, attempts to assess tissue viability in this manner have met with some success. The requirement for dye injection is however a significant barrier to the uptake of this technique. The dye itself is costly and there are risks associated with injection. Moreover, the dye has a 3-4 minute half-life and must be cleared from the blood stream before the procedure can be repeated. This takes 10-15 minutes, which makes this technique unsuitable for use in situations in which quick repeat scans are necessary or in which dynamic changes need to be followed. Finally, ICG images are collected and then generally processed offline, which makes it difficult to provide a real-time indication of tissue viability.

It is known to measure blood perfusion by observing the scattering of monochromatic and coherent light from blood cells moving in illuminated tissue. Laser light that is incident on tissue, typically the skin surface, is scattered by moving red blood cells and undergoes frequency broadening. Two basic coherent imaging techniques are used to analyse this effect: laser Doppler and speckle contrast. Using the laser Doppler technique, the frequency-broadened laser light scattered from moving cells, together with laser light scattered from static tissue, is detected and the resulting photocurrent processed to provide a measurement of the average frequency shift that correlates with blood flow. Laser speckle contrast imaging (LSI) is based on the laser speckle phenomenon in which coherent laser light interferes constructively and destructively due to the phase differences of light scattered from different parts of a surface or three-dimensional structure. If the structure is static, the speckle pattern of scattered light will be static; if the structure varies (as with blood cells moving through the microvasculature of tissue), the speckle pattern will move. To characterise the speed of movement, the image is collected over a small exposure time, of the order 20 ms. The integrated light intensity over this time period will therefore appear blurred for fast-moving structures and show good contrast for slow-moving structures. In other words, the contrast in the pattern is high for low blood-flow areas and low for high blood-flow areas. A blood flow index may therefore be derived from the average value of intensities measured within a grid (for example, 5×5 or 7×7) of pixels divided by their standard deviation. Extending the blood flow index to cover a surface area enables a two-dimensional image of blood perfusion to be recorded.

Laser Doppler imaging has been used to demonstrate that, post-operatively, blood perfusion measurements can provide an earlier indication of flap failure than is achievable by clinical observation alone. However the technique has not entered routine use due to several factors, including slow speed and the relatively complex setup required.

LSI requires analysis of a large amount of data and, accordingly, applications have developed as processing speeds have increased. With modern, fast PCs, blood flow images can be obtained at video frame rates. It was initially applied to assess blood flow in very small areas, for example the retina. More recently, information regarding cortical blood flow in the brain, liver and other areas has been extracted using this technique.

Despite the apparent advantages of LSI over ICG imaging, there has been no successful application of LSI to measure blood perfusion during an operation. The primary reason for this is that subject motion can seriously corrupt an image: movement artefact is impossible to distinguish from genuine changes in blood flow. Successful LSI imaging to date has only been carried out in a laboratory setting in which the subject can be held stationary.

There is a perceived need to provide a system that is capable of applying the LSI technique in order to image blood perfusion in tissue during an operation. If blood flow images could be collected at video frame rates, this would enable tissue viability to be assessed in real time, offering the surgeon the opportunity to take action to reduce the likelihood of post-operative complications. It is known that poor perfusion through a section of a flap used in breast reconstruction can lead to a number of post-operative complications: delayed wound healing, infection, lumps due to fat or skin necrosis, etc. Avoiding these complications would significantly improve patient outcomes. On paper, assessment based on LSI would not be subject to the disadvantages of the currently-used ICG technique: the enforced delay between repeat measurements that follows from the need for dye clearance from an earlier use; and the inconvenience of and risks associated with intravenous injection.

It should be noted that autologous reconstruction is not limited to plastic surgery on the breast, although this is by far the most common application. For example, ear reconstruction has been achieved using cartilage harvested from a patient's ribs. The imaging techniques described in this application with reference to breast reconstruction are applicable to all operations in which blood perfusion through tissue is an indicator of tissue viability for reconstructive surgery.

Furthermore, although the primary spur to the development of an imaging system based on LSI is for use in tissue assessment during reconstructive surgery, the present invention will be advantageous in a wide range of clinical applications. These include other surgical procedures, burns assessment and wound care.

The present invention accordingly provides an optical coherence imager comprising:
  a laser source for illuminating an area of tissue surface;
  a detector system comprising an array of detector elements capable of operation at video frame rates, the detector system being arranged to detect laser light scattered from the tissue surface and to generate laser output signals indicative of scattered light intensities;
  signal processing apparatus arranged to read the laser output signals generated by the detector system and, from these signals, to generate an optical coherence image and to further process selected one or more optical coherence images to form a representative image of blood flow within the tissue; and
  a display screen adapted to display the representative blood flow image; wherein
  the selected one or more optical coherence images are those obtained from output signals that are generated by the detector system only during a time period that is designated a stable time segment;
  the stable time segment is selected, during imager operation, from a plurality of tested time segments, each tested time segment corresponding to different time-domain subsets of a period of imager operation; and
  each tested time segment is assessed by extraction of stability indicators from a Fourier Transform analysis of time-varying values extracted from a region of interest within the illuminated tissue surface area that extends spatially over a number of image pixels.

In another aspect, the invention provides a method of identifying a stable time period during acquisition of an optical coherence image, the method comprising:
  a. Identifying a region of interest that extends spatially over an array of image pixels;
  b. Identifying one or more tested time segments, each tested time segment corresponding to different time-periods of image acquisition in which a number of successive image frames are taken;
  c. for each frame within each respective tested time segment, calculating a spatially merged value of detected signals within the region of interest;
  d. For each tested time segment, calculating the Fourier Transform of a time series of the spatially merged values to form a power spectrum and extracting one or more stability indicators therefrom;
  e. Comparing the one or more stability indicators from each tested time segment and selecting the tested time segment whose stability indicators best match predetermined criteria; and
  f. Identifying the time period of image acquisition of the selected tested time segment as the stable time period.

Examples of optical coherence imagers include laser speckle imagers and Doppler imagers. Such imagers have, to date, been found to provide useful imaging capabilities in a number of fields. The apparatus and method of this invention will be advantageous in any imaging environment in which it is difficult to exclude movement artefact from the image. To counter movement artefact, this invention includes a technique to examine the image as it is collected and to identify image frames that were collected during a period of stability. Once identified, these more stable image frames are used to generate a representative coherence image, with reduced movement noise. This invention will be particularly beneficial to, for example, the clinical field in which it is hard to avoid patient movement. Heartbeat inevitably induces movement in a subject, which may obscure meaningful data. The immediate requirements of surgery must take precedence over holding the patient still and so, in such situations, tissue movement may corrupt the scan results. Moreover, it may also be difficult to maintain the stability of the scanning apparatus. Potential surgical applications of this invention include: reconstructive plastic surgery; intra-operative assessment of skin blood flow during vascular and endo-vascular reconstructive surgery (an increasing problem with increasing age, diabetes and metabolic syndrome); and abdominal surgery, for example to determine the part to excise from a section of colon with necrosis. The invention also has potential to provide a screening technique to assess the risk of pressure ulcers prior to surgery, for burn assessment and for wound care in general.

The invention also provides a method of assessing tissue viability potential including the steps of:
  a. Generating a representative optical coherence image of body tissue in accordance with the method described above;

b. Using values generated for the representative coherence image and spatial location of regions within the tissue image, determining an indicator of tissue viability potential for each region in terms of predetermined assessment criteria that inform on the potential of the tissue to develop post-operative complications of predefined severity; and c. Displaying the representative image with each region displayed in a colour selected in accordance with the indicator of tissue viability potential determined for that region.

The invention will now be described, by way of example only, and with reference to the accompanying drawings, in which.

Figure 1:
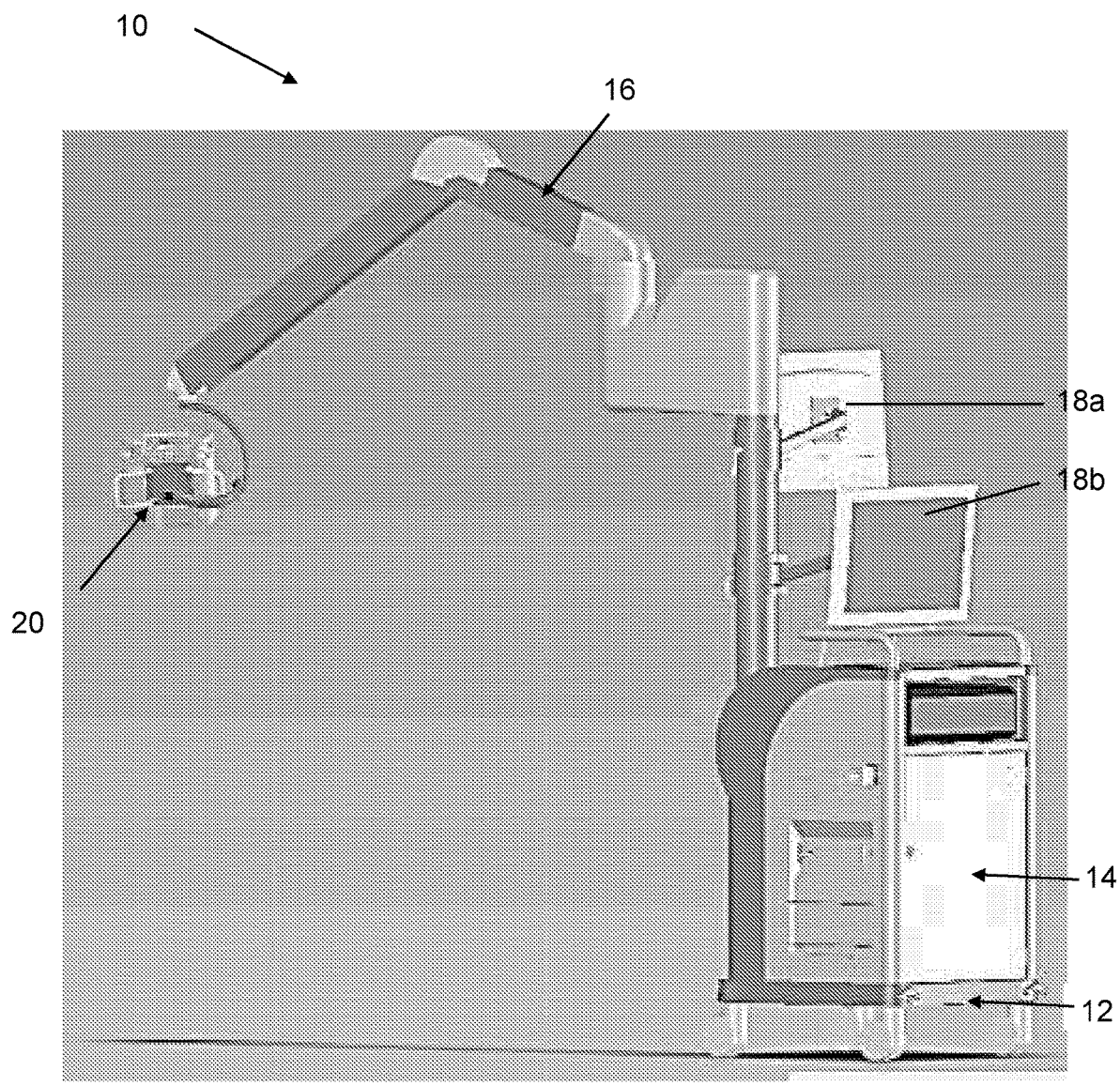
FIG. 1 is an overview of a system for laser speckle imaging, incorporating elements of this invention.

With reference to FIG. 1, there is shown an overview of a system for laser speckle imaging. The apparatus 10 comprises a mobile, lockable stand 12 that supports an enclosure 14, a long-reach flexible arm 16 and two display screens 18a, 18b, one for operator use (if required) and the other for surgeons use. The flexible arm 16 carries a laser speckle imaging (LSI) scan head 20. The enclosure 14 contains a computer, which is arranged to analyse data received from the LSI scan head and to output the results to the display screens 18a, 18b. It also provides space for a power supply and isolation transformer to power the LSI scan head 20, computer and screens 18a, 18b. Optionally, a printer is provided for printing a hard copy of the results.

In use, the surgeon, or other operating theatre personnel, wheels the stand into the vicinity of the patient and locks one or more of its wheels to maintain the stand at its required position. This will be close enough to the patient to enable images to be taken but sufficiently removed that it will not interfere with the essential procedures of the operation. The operator will then manoeuvre the LSI scan head 20 such that it lies close to and is directed towards the part of the patient that is to be imaged. This motion is facilitated by the long-reach flexible arm 16. More details of the arm 16 will be provided later but, for the current purpose, it is sufficient to appreciate that the arm facilitates single-handed operation, smooth movement, three-dimensional angulation of the scan head 20 and its reach is such that it can be extended across the operating table. Moreover, once positioned, the LSI scan head 20 is held securely and stably, without the need for locking detents or clamps, and is not prone to wobble or drift.

Figure 2:
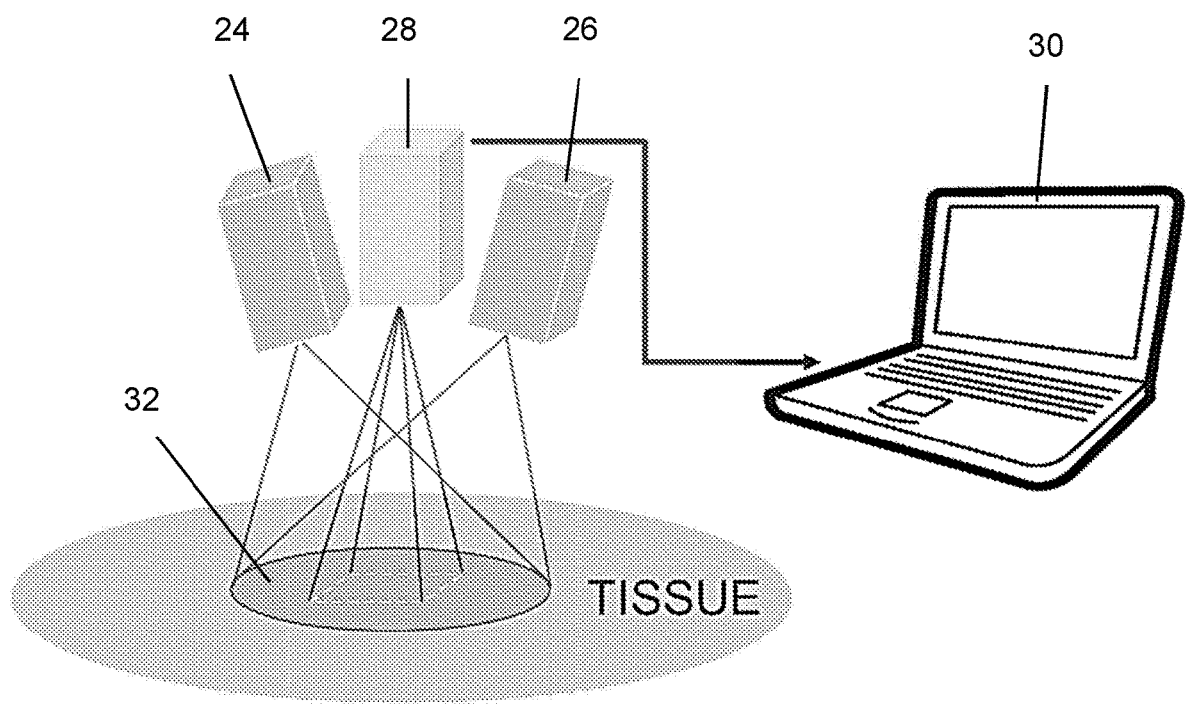
FIG. 2 is a schematic illustration of an embodiment of laser speckle imaging apparatus in accordance with this invention.

Once the LSI scan head is in position, images of the patient tissue of interest can be taken. FIG. 2 shows the elements of the LSI scan head required to take the images: a low-power near infrared laser 24, a polychromatic light source (RGB LED) 26 and a detector system 28 that is sensitive to visible light and also to light of the laser wavelength. Signals from the detector 28 are communicated to the computer 30 for analysis. The computer 30, as indicated previously, is located within the enclosure 14 and remote from the scan head 20.

Light from both the laser 24 and RGB 26 sources is directed by lenses (not shown) to illuminate a section of tissue surface 32. Light reflected from the surface 32 is directed to the detector system 28, which comprises an array of detector elements to provide spatial resolution. Each element is sensitive to the red, green and blue components of light from the RGB LED 26 and to near infrared light from the laser source. The computer 30 analyses the signals detected at each element to extract the required information for each pixel in an image. Images are output to the display screens 18a, 18b and used to guide the surgeon during an operation.

In this embodiment of the invention, detector elements are sensitive to all illuminating wavelengths. When taking images therefore, the illuminating source is cycled: laser light then each component of light in turn from the RGB LED source 26. This enables data relating to each source wavelength to be readily separated for analysis. Alternatively a blocking mechanism may be used. For example, in another embodiment, the laser source is on continuously but blocked using an infrared filter when the RGB sources are cycled to take a colour photo image.

Blood flow measurements are extracted from data obtained from a speckle contrast analysis of light detected from the laser source. When laser light is scattered back from moving blood cells near the tissue surface 32, it creates a speckle pattern. When imaged for short exposure periods therefore, speckles created by reflection from slow-moving blood move relatively little and therefore show good contrast. Over the same exposure period, speckles reflected from tissue parts with fast-moving blood move to a greater extent, blurring the speckle pattern. In using the speckle contrast method to image blood perfusion, it is assumed that blood perfusion is proportional to the mean velocity v of blood flow.

In order to achieve high video frame rates, the speckle patterns in this embodiment of the invention are processed spatially. That is, the contrast pattern (intensity variation) is observed over small sub-groups (5×5) of pixels within the image frame and, for each sub-group, a value of the speckle contrast K, equal to the ratio of the standard deviation of the pixel intensities within the group to their mean intensity, is derived. The speckle contrast image is simply a representation of the variations in the value of K over all sub-groups within the detector field of view. Conventionally, a red colouring is used in the image to indicate high blood flow or high perfusion and blue indicates low blood flow or poor perfusion. Other colours, in rainbow sequence, indicate various intermediate levels of perfusion. For such spatial processing, the detector system 28 must comprise significantly more detector elements than the number of pixels required in the speckle contrast image.

Following the assumption that blood perfusion is proportional to the mean velocity v of blood flow, it is apparent that perfusion is inversely proportional to the correlation time $\tau_c$ of photons within the tissue. Mathematically therefore, the speckle contrast K may be derived from the following equation:

$$K = \frac{\sigma}{\langle I \rangle} = \left\{ \frac{\tau_c}{2T} \left[ 1 - e^{\left(\frac{-2T}{\tau_c}\right)} \right] \right\}^{1/2}$$

where T is the integration time of the camera; and
the correlation time $\tau_c$ is given by: $\tau_c = 1/(ak_o v)$ where:
a is an unknown factor related to the Lorentzian width of the scattered spectrum and the scattering properties of the tissue,
v is the mean velocity and
$k_o$ is the input light wave number.

The above equation can therefore be used to relate speckle contrast K to tissue perfusion. The speckle contrast can vary between 0 (no speckle, very high perfusion) and 1 (fully developed speckle, very low perfusion).

A Flux image is then generated, which inverts the speckle contrast value K, such that the value of the parameter used to form the image is more directly related to perfusion:

$$\text{Flux} \propto \left( \frac{\langle I \rangle}{\sigma} \right)^2$$

In most embodiments of this invention, the computer 30 also generates a DC (intensity) image. This is simply the average intensity for each 5×5 pixel area used to generate the Flux image.

The speckle contrast image will not, in itself, present the surgeon with immediately apparent guidance. The perfusion image must be aligned with a photographic or video image of the tissue under examination. In this way, the surgeon can readily identify which areas of tissue have high perfusion and therefore have greater viability. In this embodiment of the invention, the RGB LED sources 26 are switched in sequence to take video images in each of the red, green and blue illumination bands. The computer 30 merges the detected relative intensities to generate a colour image. Because the same detector elements are used to record images at all illuminating wavelengths in closely spaced sequence in time, a contemporaneous pixel-by-pixel matched colour photographic record of the sampled tissue is generated.

The computer 30 displays both the photographic and perfusion images on the same display screen 18a, 18b for easy reference by the operating theatre personnel.

In alternative embodiments, separate detector elements, sensitive to different spectral bands may be used in close proximity to each other. The proximity is required to enable the perfusion image to be aligned with the photographic image. This embodiment may be preferred if, for example, the laser 24 emits in the near-infrared and the detector elements are not so sensitive to this wavelength. Better speckle contrast resolution can be obtained using infrared rather than visible light. Moreover, data may be collected more rapidly if there is no longer any need to switch between sources, enabling images to be displayed at a higher frame rate.

As will become apparent, perfusion imaging in accordance with this invention does not give rise to instantaneous video-rate images. Rather, it provides a representative image from data accumulated over a period of time, generally of the order of a few seconds. Under these circumstances, video-frame rate colour optical images may be unnecessarily data-intensive. In alternative embodiments therefore, grey-scale photographic images are used to assist alignment. A pair of images, taken, for example, at the start and end of perfusion-image acquisition should be sufficient to align visible features with the perfusion image.

The use of LSI in the assessment of tissue viability has many advantages over prior art methods not least its ability to acquire continuous real time images at video frame rates. However, this capability is irrelevant if the image quality is so low that useful information cannot be extracted. As noted previously, the principal bar to LSI being used to assess tissue viability is its sensitivity to movement. Relative motion between the LSI scan head 20 and the patient is indistinguishable from changes in blood flow rates. The use of a stable platform 12 and particularly stable design of long-reach arm 16 reduces the potential for movement of the LSI scan head 20 however this does not address the problem of patient movement, nor of physiological factors that affect the perfusion image. A novel approach to this problem that is adopted by the present invention is to analyse data that is collected from a selected group of pixels within the detector field of view over an extended period of time. This data is broken up in the time domain into segments, each segment corresponding to a predetermined time period within the extended collection period. Scattered laser intensities detected within the selected group of detector pixels and within each time segment are averaged spatially and analysed temporally to provide an indication of the stability between scan head 20 and the tissue it was observing when that data was collected. In deriving the speckle contrast measurement over the whole image, the only data used from the extended collection period is that which was collected within the time period that is identified as corresponding with the most stable segment, or within a segment of acceptable stability. That is, the speckle contrast image is effectively a representative image of the contrast over the extended period of time, derived from only a subset (in the time domain) of data that has been determined to be collected at a time of stability.

Figure 3A:
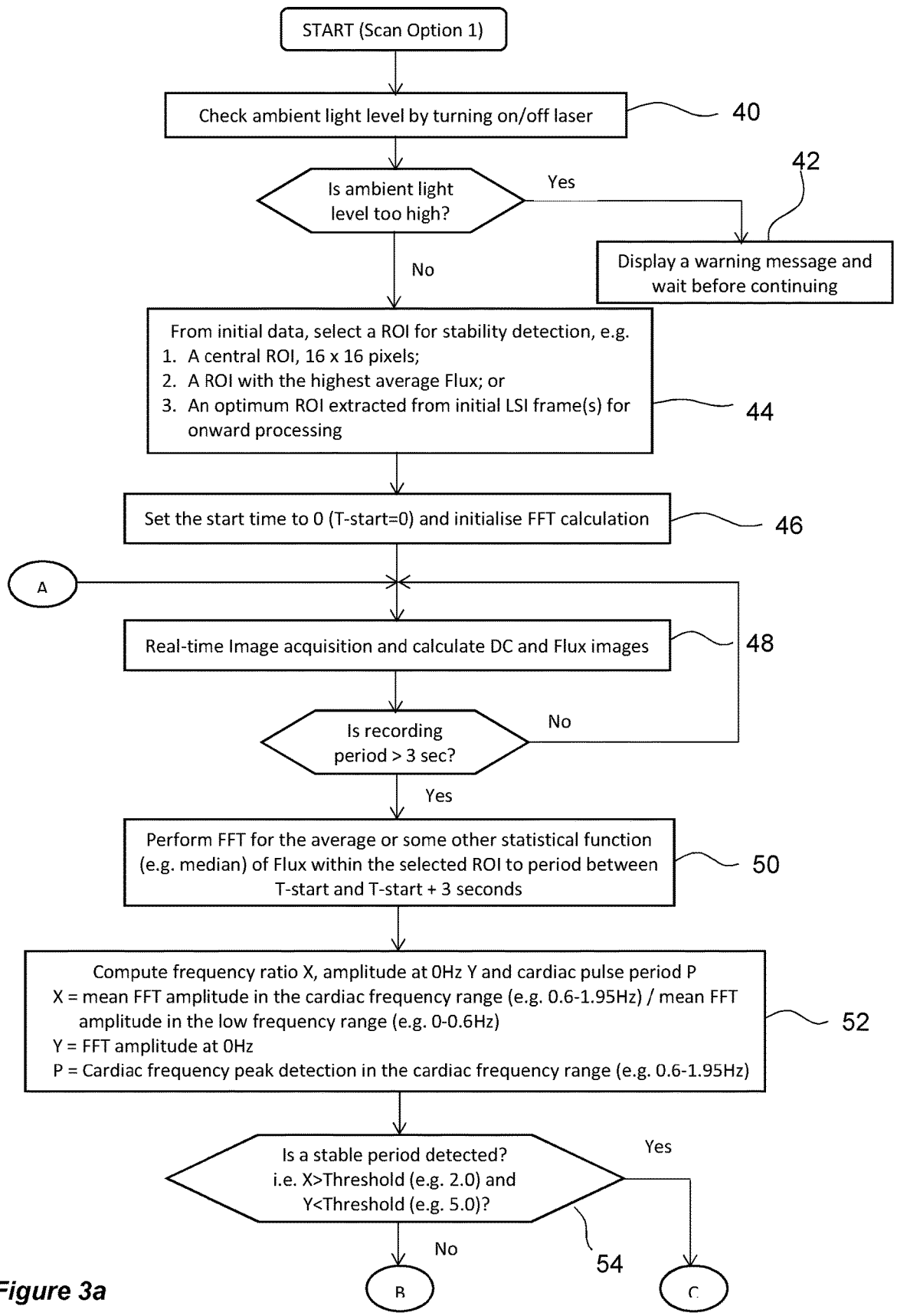
FIGS. 3a and 3b show a flow chart representing a first embodiment of a stability algorithm for use with an LSI embodiment of the coherence imager of this invention.
Figure 3B:
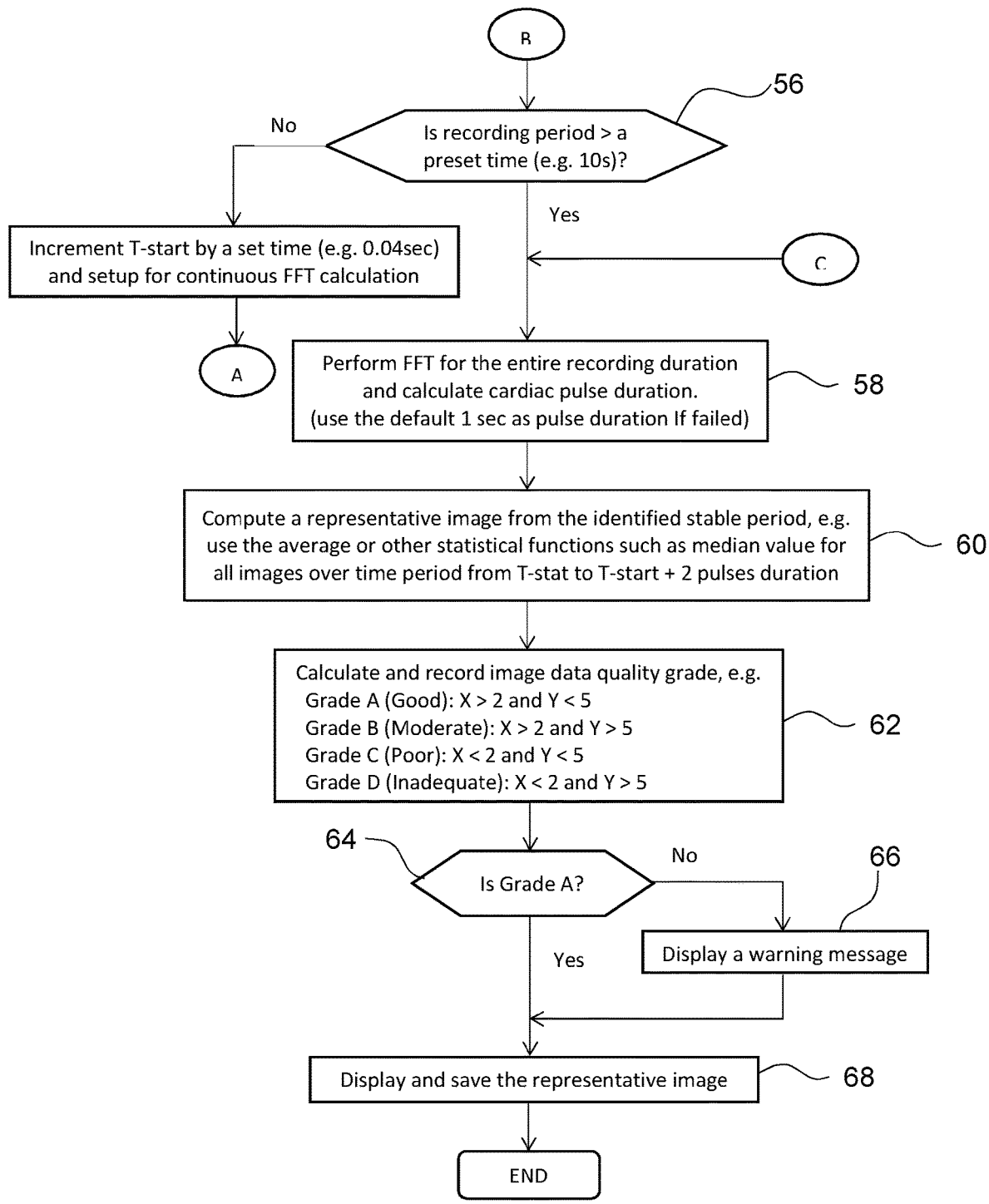

FIGS. 3a and 3b illustrate, by way of a flow chart, a first implementation of an algorithm (Scan Option 1) for detecting the time interval during an extended collection period at which the patient tissue and scan head were held in the most stable relative orientation. Unless indicated otherwise, the process steps are all carried out by the computer 30 at the time of image acquisition.

At a first step 40, the ambient light level relative to that of the laser light is checked by noting the increase in detected signal when the laser is switched on. If the ambient light level is too high, the signal from the laser is too low for the discrimination required. Accordingly, the process is stopped and a warning message sent 42 to the display screens 18a, 18b to alert the operator and/or surgeon.

Otherwise, the process continues and an initial set of one or more perfusion image frames are collected. The next step is to select 44 a region of interest ("ROI") for stability detection. This is the area of the field of view from which data will be analysed to determine stability. This could be selected by a number of methods but for this embodiment of the invention, selection is on the basis of a single static image. Accordingly, if the initial data set includes more than one image frame, pixel values are averaged to generate an average perfusion image frame. A simple example of ROI selection is simply to take a central area of, for example, 16×16 pixels in the Flux image. Alternatively, the detector signals from across the field of view could be compared to find a 16×16 pixel region that has the signal with the highest average Flux. A third, and preferred, alternative is to assess several potential ROIs to determine which has the most promising parameters for stability determination. One example of potential ROI selection is to take five potential 16×16 pixel ROIs from within a central image area. For each potential ROI, both the average Flux value of the 16×16 pixel area and the DC standard deviation (DC std) are calculated. It will be recalled that each DC image pixel is generated from the average intensity of the same subgroup of data pixels from which each perfusion or Flux image pixel is derived. The DC std for the 16×16 pixels within each ROI is accordingly derived from the pixel intensities within the DC image. The DC Std provides an indication as to whether the ROI includes a flap boundary: a high value reflecting a large intensity range within the ROI. The optimum ROI from among those identified as potential ROIs will be that which best satisfies certain criteria. For example, the highest average Flux and a DC std of less than 10% of its average DC intensity. Selecting the ROI in this manner has two major benefits. First, the higher average flux increases the likelihood of obtaining good quality data in which to find a period of stability and the DC std criterion helps to avoid edges of flaps, gauze and other dressing or padding materials.

Once the ROI is selected the, at step 46, the start time ($T_{start}$) is set to 0 and Fast Fourier Transform (FFT) calculation initialised.

The LSI system 10 is then run 48 in its standard operating mode to take both a DC (intensity) image and Flux (speckle contrast) image from detected scattered laser light. Image acquisition is continuous from this point and data collected is stored by the computer 30 in an accessible memory. After at least 3 seconds of data collection/image recording, data from the ROI only is extracted and an average value of the Flux determined over the 16×16 pixel area for each recorded frame within a 3 second period of image acquisition. Alternatively, another statistical function such as the median value within the 16×16 area can be used. In any case, some averaging function is applied to the ROI to give a representative average Flux measurement for each recorded frame. Thus, for a standard video imaging rate of 25 Hz, this will result in a time series of 75 average Flux values. In the first iteration, the 3-second time period/75 frames will correspond to the initial 3 seconds of image acquisition. In subsequent iterations, $T_{start}$ will be a value other than zero and averaging will be applied to a later subset of frames, through a period $T_{start}$ to $T_{start}$+3 seconds.

At a next step 50 the Fourier Transform of this time series is found using a FFT calculation to generate the power spectrum P(ω). This power spectrum P(ω) is then analysed at step 52 to extract three parameters: the cardiac pulse period P; the amplitude Y of the function P(ω) at ω=0, i.e. the power of the zero component; and the ratio X of power in the cardiac frequency range to power in the low frequency range.

Cardiac frequencies are generally in the range 0.6-1.95 Hz (pulse rate of 36-117 beats per minute). As the blood is pumped through the tissue, there will be a characteristic fluctuation in its motion at the frequency of the heart beat. This speed variation, in turn, affects the intensity of light scattered from the moving blood cells i.e. the light reaching the detector system from the laser source. The cardiac frequency can therefore be found by peak detection within the power spectrum P(ω) across the range 0.6-1.95 Hz. The position of the peak gives the cardiac frequency and hence the cardiac period P.

The amplitude of the zero component of the power spectrum (Y=P(0)) provides an indication of the stability of the Flux signals over the 3 seconds duration i.e. to determine the extent to which it is subject to baseline drift.

The third parameter X provides an indication of the relative contribution to the overall signal from the heartbeat and from low frequency disturbances, assumed to be patient-scan head movement. In order to derive X therefore, the FFT power spectrum P(ω) is sectioned into a cardiac frequency range (0.6-1.95 Hz) and a low frequency range (0-0.6 Hz). The average amplitude in each range is then extracted and X calculated from:

$$X = \frac{\text{mean } FFT \text{ amplitude in the cardiac frequency range}}{\text{mean } FFT \text{ amplitude in the low frequency range}}$$

If the raw data that was collected by the detector system during this period was collected during a period of comparative stability i.e. little relative motion between patient and scan head, then the value of X should be relatively high i.e. movement noise is less than that arising through the heartbeat. In conjunction with this however, it is desirable to have a low Flux signal drift. That is, Y should be relatively low.

At step 54 therefore, the values of X and Y are compared with threshold values $T_X$ and $T_Y$. This initial 3-second period of image acquisition is determined to be stable if:

$$X > T_X \text{ and } Y < T_Y$$

For this embodiment of the invention, the threshold $T_X$ is set at 2 and $T_Y$ at 5. Other values can be used if a different degree of stability assurance is required.

With reference now to FIG. 3b, if the 3-second period of image acquisition was not determined to be sufficiently stable, the process moves to step 56 and checks whether the recording period has exceeded a preset time, for example, 10 seconds. If it hasn't, then $T_{start}$ is increased by a set value, in this embodiment 0.04 seconds, and the process waits until the real time image acquisition process has enough data for a new 3 second block commencing at the new $T_{start}$. A FFT calculation is then carried out 50 on the frame average Flux values of the ROI over this new time period and the stability analysis proceeds as before. That is, the FFT is analysed 52, 54 to assess whether this new 3-second period of image acquisition represents a stable data collection period. This process continues until either a stable period is detected or a preset recording time is exceeded 54, 56.

Once the stability analysis is complete, a FFT of the average frame Flux values of the ROI over the entire period for which data has been collected is calculated. From this, more complete, data set, the cardiac pulse duration P is extracted, as before, by peak detection within the appropriate frequency band. This will give a more accurate value for the pulse rate. Nonetheless, there may be occasion in which the peak is too indistinct for detection, for example another significant contribution to noise lies within this frequency band, and so the pulse determination will fail. In this case, a default duration may be set, for example 1 second.

The detected stable period, will be the three-second period extending from $T_{start}$ to $T_{start}$+3 in which the stability criteria (X>2; Y<5) are first satisfied ($\Delta T_{stable}$). In some instances, the preset recording time will be exceeded without identification of a stable period that satisfies the stability criteria. The stable period is then taken to be that period within the preset recording time for which the stability criteria are most closely approached. For example, the period that has the lowest value of Y from all periods for which X exceeds 2. At step 60, a representative image is computed for the entire imaged area (not just the area within the ROI) from data obtained during that part of the stable period ($\Delta T_{stable}$) that extends from $T_{start}$ to $T_{start}$+2P. That is, a time frame of data collected over two cardiac pulse periods is used to form the image. For example, if the pulse period is 1.28 seconds, 64 frames of data (assuming normal video rate of 25 Hz) will be used to calculate the representative image.

For each frame of data within the two-pulse period, the perfusion image is generated as described previously. That is, a set of speckle contrast values of between 0 and 1 for each sub-group of 5×5 detector elements with the detector system is determined. This data set is then converted to a set of Flux values, which are used to form a Flux image. For each image data point, an average Flux value is found over all frames taken within the stability period. This average could be taken by any suitable statistical function, such as mean or median value. The set of averaged Flux values are used to generate the representative image.

It should be apparent that the Flux image generated by this speckle contrast method is not one that represents a snapshot in time, but a representative image of the contrast pattern range observed over a two-pulse period duration. By using a sample period that is a multiple of the pulse period flow rate variations due to heart beat are averaged out. The result is not a succession of video-rate images. A representative image may only change every 10 seconds, assuming this is the preset duration of image acquisition. However good discrimination in the time domain is of far less relevance to the assessment of tissue for use in reconstructive surgery than accurate spatial location of areas of poor perfusion.

In this embodiment of the invention, the scan period from which data is taken may not actually have satisfied the stability criteria (X>2; Y<5) as, if this is not satisfied during the time allowed, a next-best period is used instead. In this latter scenario, the representative image will not be as accurate as it could be: movement artefact will be making a greater contribution to the perfusion image. Accordingly, at step 60 an assessment of the image quality is made and displayed to the surgeon and/or operator. If the stability criteria were fully satisfied, then the image is qualified Grade A (good). If only the X threshold is satisfied (low frequency noise contributions less than those from cardiac rhythm), then the quality is Grade B (moderate). If only the Y threshold is met, then the quality is Grade C (poor). If neither are met, it is Grade D (inadequate). At step 64, a check is made as to whether the image quality is of Grade A. If it is not, a warning message is displayed 66. Finally, the representative image generated at Step 60 is displayed 68 to the surgeon and/or operator and saved to computer memory.

If the representative image is not Grade A, then the surgeon or operator may choose to repeat the procedure, or to extend the preset period for image acquisition.

Figure 4A:
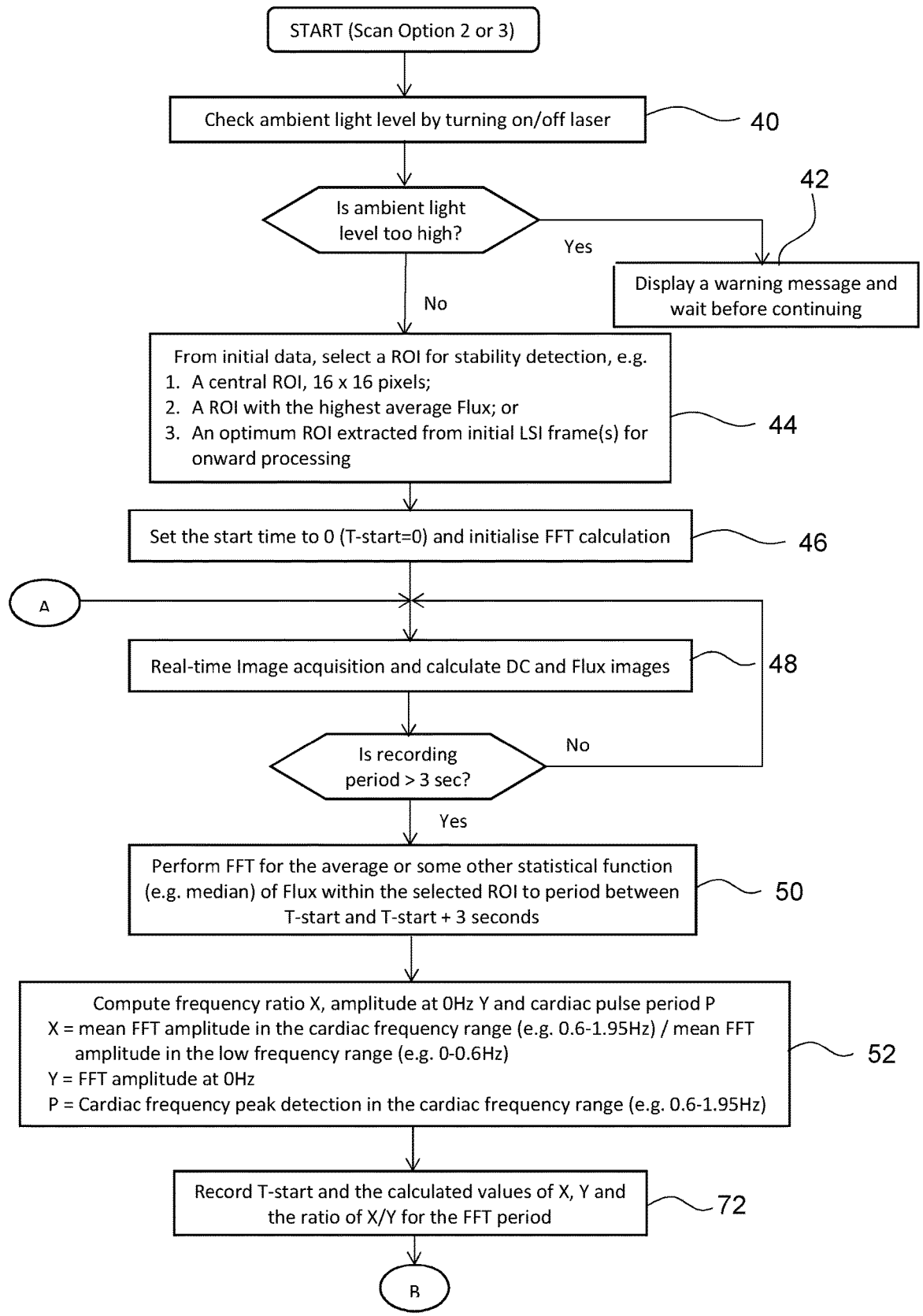
FIGS. 4a and 4b show a flow chart representing second and third embodiments of a stability algorithm for use with an LSI embodiment of the coherence imager of this invention.
Figure 4B:
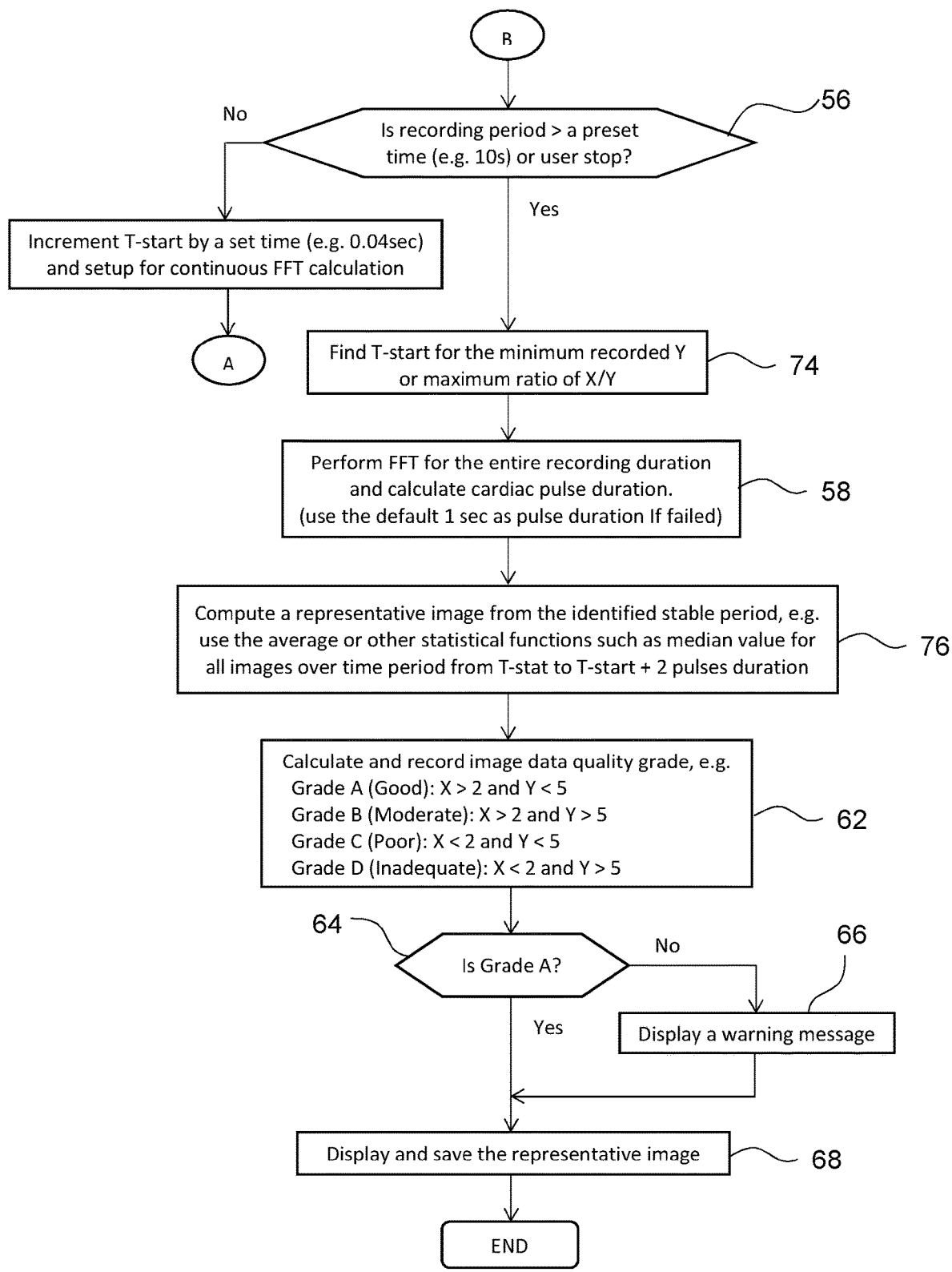

FIGS. 4a and 4b illustrate, by way of a flow chart, alternative implementations (Scan Options 2 and 3) of the algorithm for detecting the time interval during an extended collection period at which the patient tissue and scan head were held in the most stable relative orientation. Steps that are the same as those shown in FIGS. 3a and 3b are provided with the same reference sign.

Initially, these scan options proceed with the same steps as for Scan Option 1. That is, ambient light is tested 40 for the correct level before selecting 44 a ROI within the field of view for stability detection. The start time $T_{start}$ is initially set to 0 and the FFT calculation initialised 46 as real-time data acquisition and image extraction 48 begins. During later iterations, $T_{start}$ will take increasing time values. After at least a 3 second acquisition period, the Flux values derived from the ROI are averaged over the ROI area for each image frame. This gives a time-series variation of the average ROI Flux within this selected 3-second period. The FFT is then computed 50 for this time-series variation to derive the power spectrum P(ω). The cardiac pulse period P, along with stability indicators X and Y, are extracted 52 from the FFT function.

For this embodiment, on each occasion that a time segment is selected and tested for a stability indicator, at step 72, the value of $T_{start}$ and the stability indicators X, Y along with the calculated ratio of X/Y are recorded for the segment.

At step 56, a check is made as to whether the recording period has exceeded a preset time, for example, 10 seconds (scan option 2) or whether an operator instruction has been received to stop (scan option 3). If not, then $T_{start}$ is increased by a set value, for example 0.04 seconds, and the process waits until the real time image acquisition process has enough data for a new 3 second block starting at $T_{start}$. A FFT calculation is then carried out 50 on the frame average Flux values of the ROI over this new time period segment and the stability analysis proceeds as before. That is, the FFT is analysed 52 to extract the cardiac pulse period P and stability indicators X and Y.

The process continues iteratively, testing new time segments $T_{start}$ to $T_{start}$+3 seconds and recording the values of $T_{start}$ against the values of X, Y and the calculated value of X/Y for each time period.

Once the recording period exceeds a preset time or reaches a point at which the operator indicates the stability assessment should stop, the stability algorithm, in this embodiment, proceeds to an evaluation step 74. The set of values recorded at step 72 are examined 74 to find either the maximum stored value of X/Y and/or the minimum value of Y and the associated value of $T_{start}$ ($T_{max}$). This evaluation will find the 3-second period in which collected data had the lowest low-frequency noise in relation to the cardiac noise and/or lowest baseline drift.

As with the previous embodiment, the cardiac pulse period is extracted 58 from the FFT of all data gathered for the ROI during the entire image recording period (preset time or operator-indicated stop) to provide a more accurate assessment.

Following the identification in step 74 of the 3 second period after the $T_{start}$ value ($T_{max}$) with highest associated X/Y ratio, all data over the entire imaged scene that was collected from scattered laser light during the period $T_{max}$ to $T_{max}$+2P, where P is the cardiac pulse period, is used to form 76 the representative perfusion image. That is, as with the previous embodiment, a set of speckle contrast values of between 0 and 1 for each sub-group of 5×5 detector elements with the detector system is determined and used to generate the Flux image. For each image data point, an average Flux value is found over all frames taken within the stability period ($T_{max}$ to $T_{max}$+2P). This average could be found by any suitable statistical function, such as mean or median value. The set of averaged Flux values are used to generate the representative image.

Thereafter, the process continues as for the first embodiment: the image quality is assessed 62 from the values of X and Y derived for the time period ($T_{max}$ to $T_{max}$+3 seconds) in which data was collected to form the representative image; a warning is given 66 if Grade B, C or D and the representative image saved and displayed 68.

In both embodiments described above, a single ROI was selected in order to find the most stable time period during image acquisition. In alternative embodiments, two or more ROI may be selected and their collected data analysed. The assessment of the most stable period could then be based on, for example, the maximum total value of X/Y for all regions of interest. Alternatively, the most stable period is selected in the first instance for which the stability indicators X and Y for all regions of interest satisfy the threshold criteria.

The time period for the averaging of Flux images to calculate the representative image is, in both embodiments, two cardiac pulse periods. A multiple of pulse periods is required to average out variations in blood flow rates during the cardiac cycle. The selection of 2 is a compromise between obtaining a better average (provided by more cardiac cycles) and speed of image acquisition (more cycles require a longer collection time). In other applications of this invention however a different multiple may be more appropriate.

In still further embodiments, the representative image need not be extracted from averaged Flux values, but from the maximum (or minimum) recorded within the selected stable time frame segment.

In another variant, the Flux images could be recorded as for standard LSI. The above-described algorithms could then be applied off-line, after image acquisition, in order to find the optimum stable period for the recorded image sequence.

The algorithms described above find the most stable period for the duration of data collection and uses data collected within this period to form a representative image. In order to increase the likelihood of periods of acceptable stability being found in any one image acquisition period, it is advantageous to reduce the likelihood of movement of both the LSI scan head 20 and tissue being imaged. There is little that can be done for the latter, beyond sedating the patient, as required for surgery in any case. For the stability of the LSI scan head 20 however, the apparatus of this invention preferably includes a particularly stable, novel design of long-reach flexible arm 16.

Figure 5:
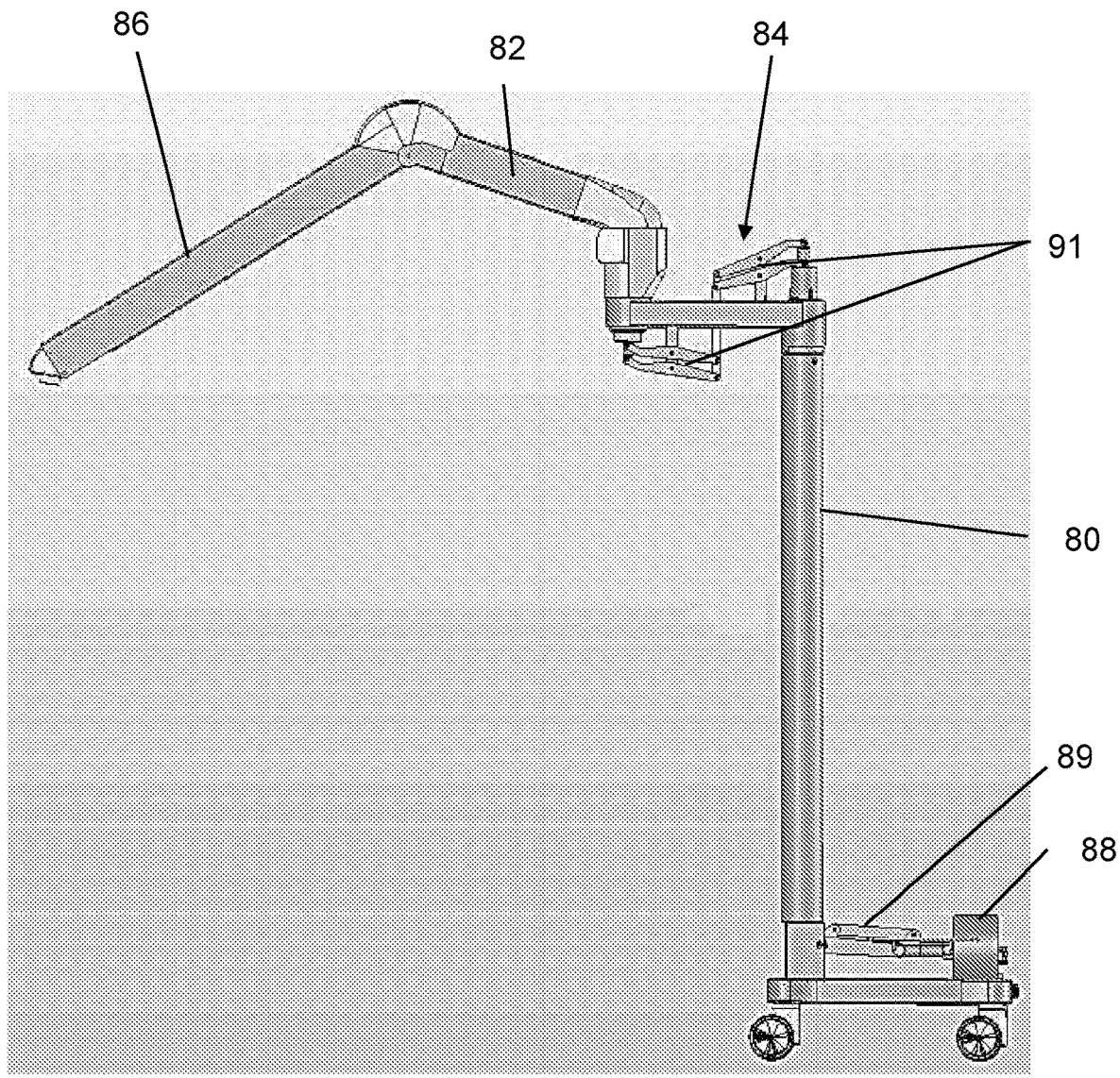
FIG. 5 is a schematic illustration of the stability arm for use with a laser speckle imager in accordance with this invention.

The arm 16 is shown in more detail in FIGS. 5 (side view) and 6 (rear view). With reference first to FIG. 5, it comprises three sections: a vertically extending section 80 in the form of a column of fixed height extending from the mobile platform 12; a first head support section 82, which is pivotally connected at its distal end to the vertical column 80 via a hinged connection with a pivotal bearing assembly 84; and a second head support section 86, which is hingedly connected to a proximal end of the first head support section 82. The LSI scan head 20 (not shown in this figure) is located at the proximal end of the second head support section 86. The arm 16 also includes a counterweight 88 located at the end of a double-arm section 89 that connects, via a series of linkage rods 90 (not shown in FIG. 5) that extend through the vertical column 80 to the bearing assembly 84.

Figure 6:
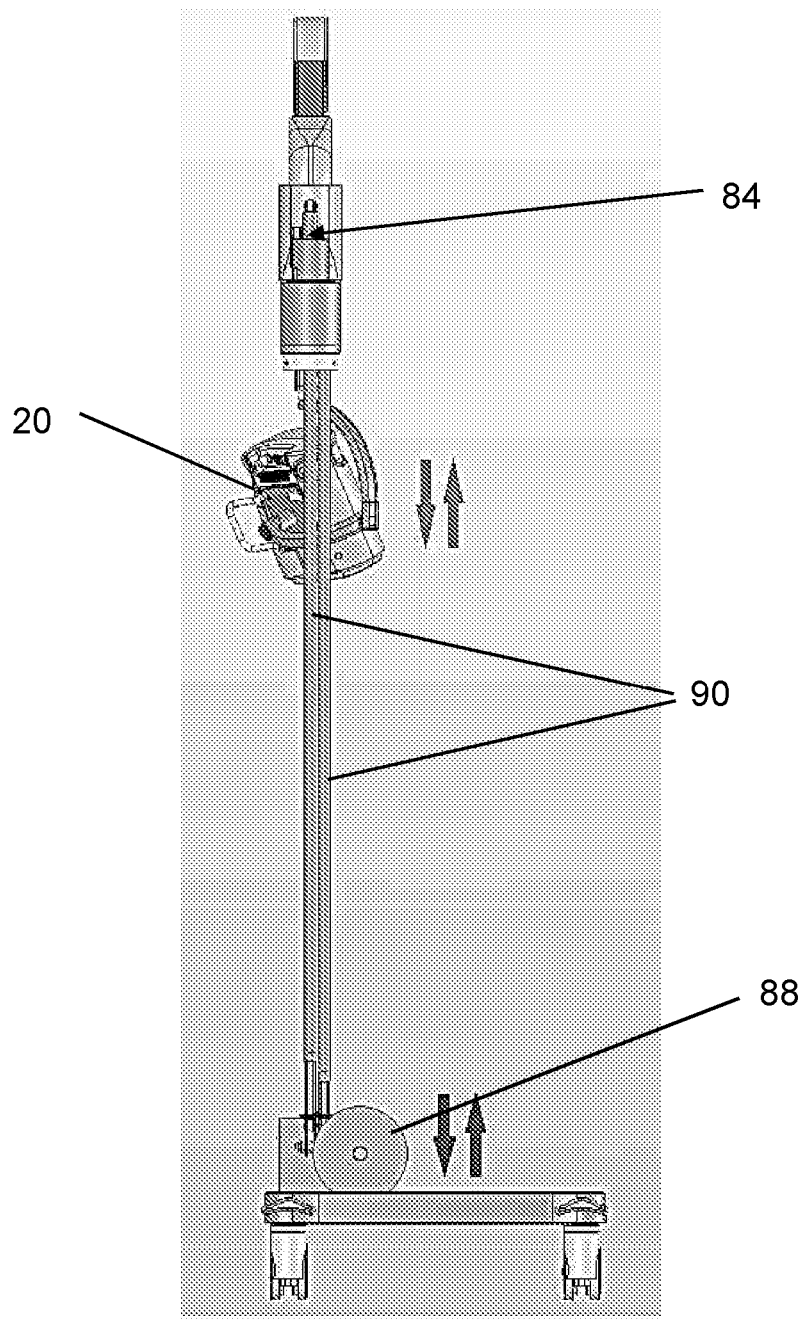
FIG. 6 is a rear view of the stability arm shown in FIG. 5, with a partial internal view showing linkage rod connections.

FIG. 6 is a rear view of the arm 16, which is illustrated with the vertical column 80 removed in order to show the linking rods 90 that connect the counterweight 88 to the pivotal bearing assembly 84. The LSI scan head 20 is also shown in this Figure. On adjustment of the scan head position 20, the first 82 and second 86 head support sections move smoothly about each other and the pivotal assembly 84 to accommodate three-dimensional movement and to allow the scan head to be appropriately positioned for a scan. Each support section 82, 86 of the arm 16 is linked to a respective lever system 91 within the pivotal assembly 84. The arrangement of levers within the assembly translates motion of the arms to an opposing movement that is communicated to respective linking rods 90 within the vertical column. This opposing movement is, in turn, communicated to the double-arm section 89 that bears the counterweight. In this way, the counterweight double arm section 89 mirrors the movement of the first 82 and second 86 head sections. The position of the counterweight 88 is therefore adjusted such that it counteracts the gravitational pull against the scan head 20. Positional stability, settling time, drifting and minor discrepancies in weight supported by the long reach arm 16 (such as variation in LSI imaging scan head weight, cabling lengths, usage of sterile barriers and the like) is compensated for by friction within the arm mechanism, counterbalance and counterweight assembly. That is, this arrangement provides a very sensitive counterbalancing mechanism, which allows fingertip movement of the scan head with minimal settling time.

The relative sizes of column 80, first 82 and second 86 head support sections are such that the position of the scan head can be adjusted over a height range of 50 to 190 cm and provide a reach that can extend over a patient on an operating table. Height adjustment over 150 cm allows the scan head to be safely moved over a shoulder position of assisting surgeons for data collection and to a sterile parking position (for example, over an instrument trolley) when not in use.

In contrast to prior art support arms, which are typically based on a system that uses spring extension and contraction, the counterbalancing mechanism of the present invention reduces both stiffness in adjustment and positional drifting.

Figure 7:
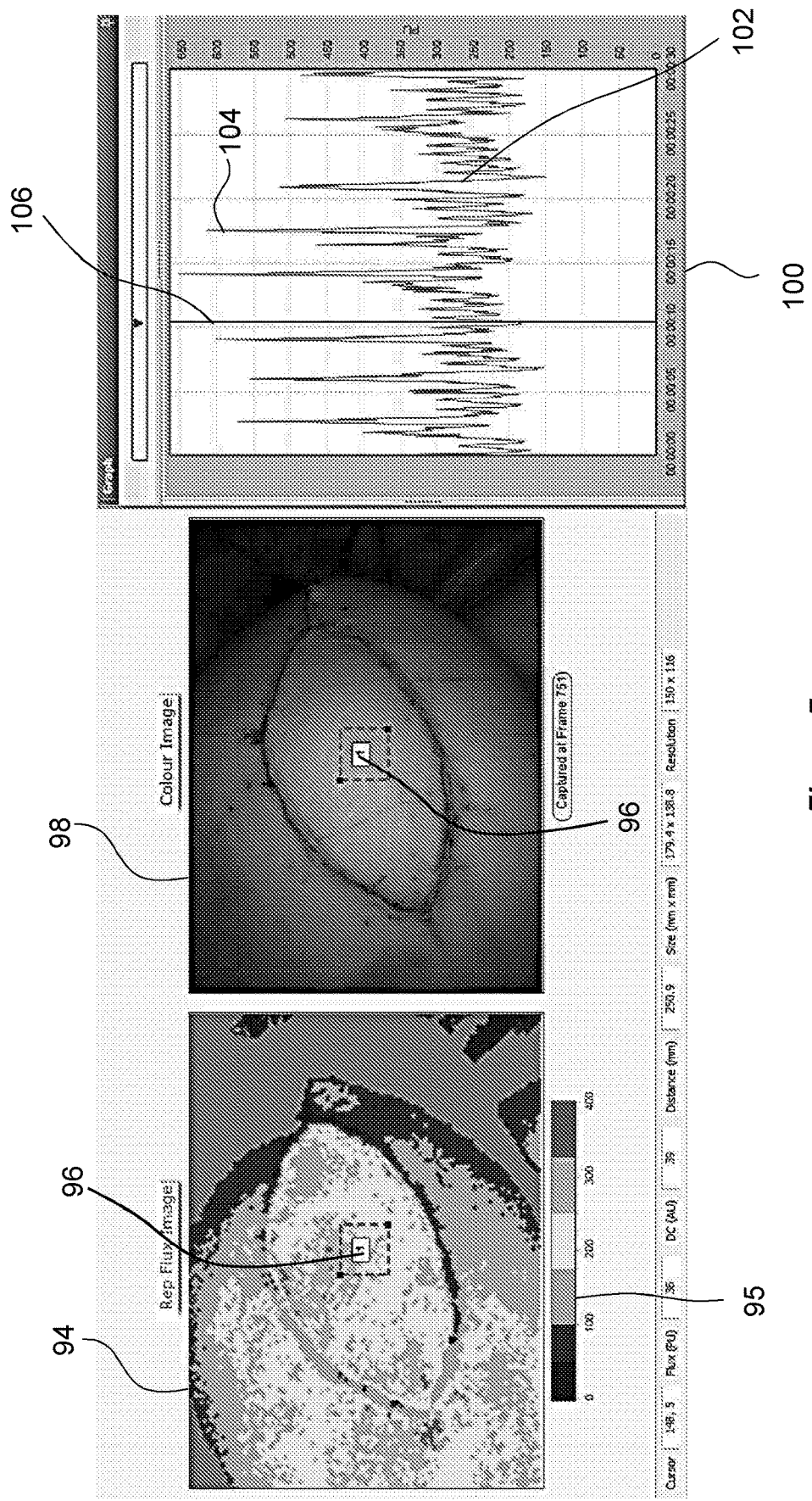
FIG. 7 is an example of a representative image with reduced pulse and movement noise obtained in accordance with this invention.

FIG. 7 shows an example of images obtained using the apparatus of this invention. A representative Flux or perfusion image 94 is shown on the left hand side. This is a representative static map obtained from a video sequence of tissue blood flow images following the method described herein. The image 94 is displayed using the conventional representation of red to indicate high blood flow and other colours following rainbow sequence down to blue, which indicates low blood flow. A colour scale 95 is shown, for information, below the image 94. The position of the region of interest (ROI) 96, data from which was used to calculate the "most stable" time period, is indicated at the centre of the flap. The perfusion image 94 is shown adjacent a colour video image 98, with ROI 96 also indicated, which was collected during the same image acquisition process.

A plot 100 to the right of the Figure indicates graphically identification of the most stable period in accordance with the algorithm described herein. The plot 100 shows a trace 102 of mean Flux values from the ROI 96 over the full image recording period. Large spikes 104 are observable in the trace, which are cause by subject (or scan head) movement. A black line 106 indicates the start of the stable period detected by the algorithm. The representative image 94 is calculated by averaging two cardiac cycles (2×0.72 s, in this instance) of blood flow images from the first frame of the stable period (indicated by the black line 106). The perfusion image 94 is therefore the best representation of data collected in the video sequence in terms of minimal noise arising from movement and with the effect of the cardiac pulse being averaged out.

Figure 8:
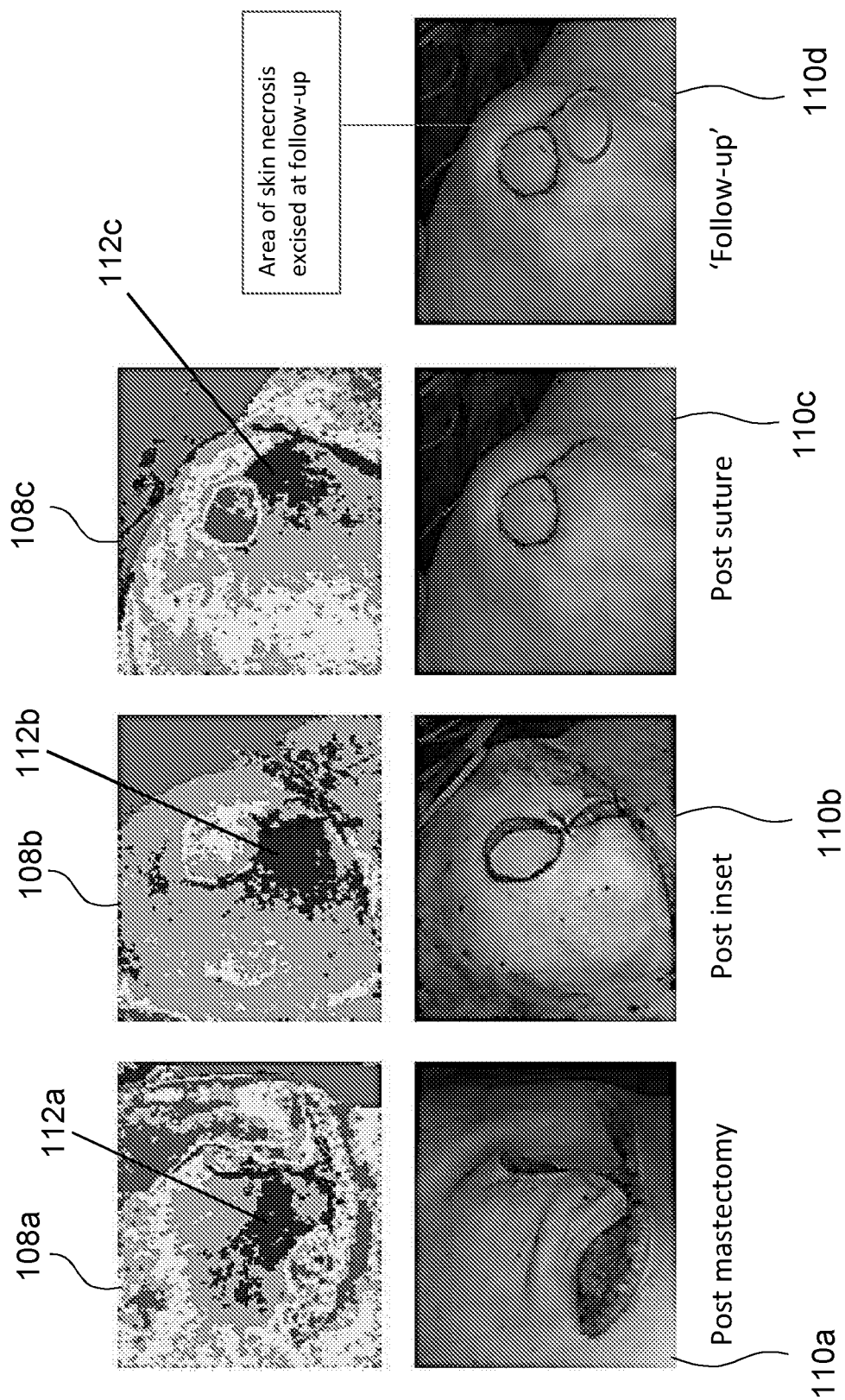
FIG. 8 is a series of perfusion images taken using apparatus in accordance with this invention shown aligned with camera images of various stages in an abdominal pedicle flap breast reconstruction.

FIG. 8 shows a series of perfusion images 108a, 108b, 108c aligned with a corresponding series of photographs 110a, 110b, 110c taken at various stages of a breast reconstruction operation using apparatus in accordance with this invention. A final optical image 110d of the reconstruction was taken several days after the initial surgery.

The perfusion images 108a, b, c use the conventional colour representation, as used for the image 94 of FIG. 7.

The first images 108a, 110a are taken after the mastectomy operation. A blue area 112a in the perfusion image 108a shows an area of low skin blood flow in the lower medial quadrant of the left breast envelope. This blue area 112b 112c persists throughout the operation: both post inset 108b, 110b and post suture 108c, 110c. The final optical image 110d shows the position of excision required due to subsequent skin necrosis. The correlation between the low blood flow region and necrotic area that had to be excised is apparent.

The FIG. 8 images indicate one potential use of this invention: to identify areas of low blood flow and that are therefore more likely to be a cause of post-operative complications. Instead of displaying a conventional perfusion image 94, 98 to the surgeon and/or operator, a different colour representation may instead be used to indicate a "viability potential". This potential would acknowledge that, in its current state, the imaged tissue is vital and informs on its potential to remain vital after reconstructive surgery. Studies have shown that there is a correlation between blood flow and clinical assessments with intra- and post-operative complications and wound healing. It looks likely therefore that a appropriate definition of "viability potential" in terms of blood perfusion measurements may prove a useful tool.

The basis of a tissue viability potential (TVP) is a definition of various levels of blood flow that correspond with respective absences of post-operative complications (POC) of varying severity. For example:

POC0: no post-operative complication;
POC1: flaps developed minor complications (defined as those without the need for revision surgery);
POC2: flap developed major complications requiring major surgery, but recovered after revision;
POC3: complete flap loss.

Blood flow ranges indicative of each POC level can be derived from statistical analysis of localised areas of low and high perfusion when comparing average flux levels for cases that went on to develop POC and those that did not. For example low perfusion at the site of the flap perforator is more likely to lead to a major POC affecting the whole flap, whereas other low-perfusion localisations may risk less serious complications. That is, the same measured perfusion level may be determined as being POC3 if at the site of the flap perforator but may only correspond to POC2 in another region of the flap.

Regardless of the definition, it is clear that different regions with viability potentials that are within different threshold levels can simply be displayed in different colours, with sensitivity to specific complications defined for each.

Figure 9:
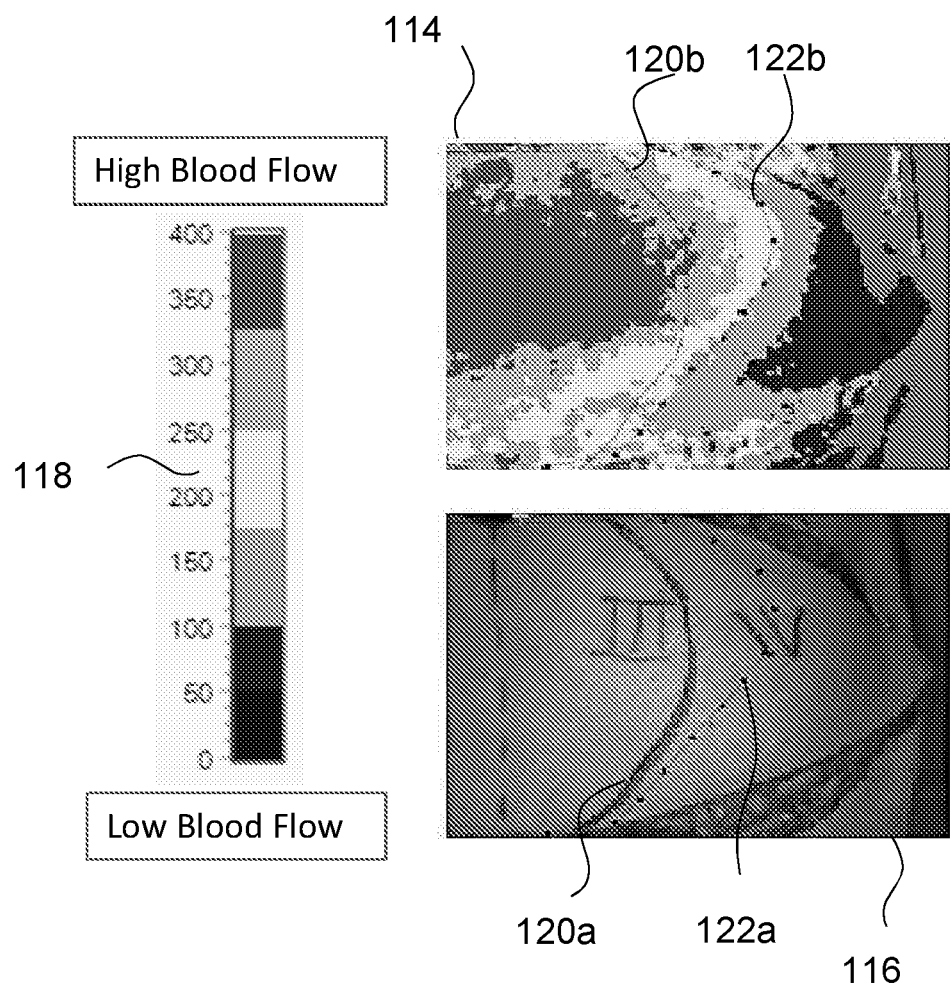
FIG. 9 is a further example of a perfusion image taken using apparatus in accordance with this invention shown aligned with a camera image of a skin flap during skin sparing mastectomy.

FIG. 9 shows a perfusion image 114 aligned with a colour photograph 116 taken as the surgeon is selecting tissue to form the flap for use in breast reconstruction. An example of a palette 118 to indicate POC thresholds that is used to display the representative image 114 is shown to the left. Blue and dark blue (<100PU) regions in the image 114 indicate poor tissue viability, which is most likely to cause post-operative complications. Pink and red regions indicate high tissue viability or low risk of POC.

The viability thresholds are determined from Receiver Operating Characteristic (ROC) curve analysis based on the use of different thresholds to assess specificity and sensitivity at POC prediction for each category of severity.

The optical image 116 of FIG. 9 shows the boundary of flap zones 3 and 4 compared with the viability image 114. The flap shape initially outlined by the surgeon, without the aid of the viability image 114, is shown in inked line 120a, 120b on the images 116, 114. The viability image 114 however indicates that significantly larger portion of the tissue area has good perfusion. That is, the surgeon could use a larger flap, indicated by the dotted line 122a, 122b in the images, which retains the same likelihood for proper healing and avoiding post-operative complications.

In this example of breast reconstructive surgery, it is apparent that the present invention enables the identification of areas of low perfusion for each patient, individually, according to their own physiology rather than to a zonal template. Such areas, once identified, may be discarded or subject to certain procedures known to improve the tissue blood flow. The apparatus of this invention has the capability to provide intra-operative, real time, non-invasive assessment of tissue blood flow as an aid to surgical decision making in the selection and use of tissue for breast reconstruction by flap or implant surgery.

In the example shown in FIG. 9, the line 120a marked by the surgeon is indicated 120b in the flux image. In order to provide this capability, this embodiment of the invention is provided with the capability of freezing a Flux image and following movement through a subsequent sequence of live images in order that a mark on the live image can be transferred to an appropriate position on the Flux image.

As indicated previously, the computer (30) sections each frame of collected data into 5×5 pixel areas. For each such subgroup (5×5 pixels), a laser speckle contrast value is derived along with an average intensity value. The laser speckle contrast values are used to generate the Flux image for that frame; the average intensity values generate the DC image. For the same frame of collected data therefore, the DC image corresponds spatially with the Flux image.

In accordance with this invention, the computer (30) generates a representative Flux image from a time-series of Flux images. In a similar manner a reference DC image is generated using the same averaging method from the same frame series, only in this instance applied to the time-series of DC images. In certain embodiments of this invention, motion of a mark that is visible in the representative DC image is mapped to an equivalent movement in the representative Flux image.

In order to achieve this mapping, a cross correlation of a live DC image with the reference DC image is calculated. Specifically, a central 21 wide-line-average pixel group from the reference image is cross-correlated with 11 sets of 21 values similarly derived from the live image, each respective set of 21 values being derived from successive pixel lines starting at 5 pixels before the line-average in the reference image. A peak in the cross-correlation values provides an indication of the degree of movement. This technique enables a shift of 5 pixels to be detected in any single period.

A special sterile marker pen may be given a characteristic tip that can be identified by image processing software. This will enable its movement to be tracked in the DC image and so the line traced on the tissue surface can be transferred to the representative Flux image.

As will be appreciated by one skilled in the art, there are many variations or additions that could be made to the embodiments of the invention that are described herein. In one alternative, the data gathered during RGB LED illumination may be used to extract more than just a video image that corresponds with the tissue perfusion image. For example, tissue oxygenation images may be generated from indicative parameters such as oxygenated and deoxygenated haemoglobin concentrations or oxygen saturation based on reflectance technology, as described in WO 2011/070357.

The invention claimed is:

1. An optical coherence imager comprising:
    a laser source (24) for illuminating an area of tissue surface;
    a detector system (28) comprising an array of detector elements capable of operation at video frame rates, the detector system (28) being arranged to detect laser light scattered from the tissue surface and to generate laser output signals indicative of scattered light intensities;
    signal processing apparatus (30) arranged to read the laser output signals generated by the detector system (28) and, from these signals, to generate an optical coherence image and to further process selected one or more optical coherence images to form a representative image of blood flow within the tissue; and
    a display screen (18a, 18b) adapted to display the representative blood flow image; wherein
    the selected one or more optical coherence images are those obtained from output signals that are generated by the detector system (28) only during a time period that is designated a stable time segment;
    the stable time segment is selected, during imager operation, from a plurality of tested time segments, each tested time segment corresponding to different time-domain subsets of a period of imager operation; and
    each tested time segment is assessed by extraction of stability indicators from a Fourier Transform analysis of time-varying values extracted from a region of interest within the illuminated tissue surface area that extends spatially over a number of image pixels.

2. The imager of claim 1 wherein the time-varying values extracted from the region of interest are merged spatially prior to calculation of the Fourier Transform.

3. The imager of claim 2 wherein the time-varying values are averaged spatially over the region of interest.

4. The imager of claim 1 wherein the stable time segment corresponds to the first tested time segment in which the stability indicators satisfy pre-defined criteria.

5. The imager of claim 1 wherein the stable time segment corresponds to the tested time segment in which the stability indicators best meet pre-defined criteria.

6. The imager of claim 1 in which the stability indicators include a ratio of an average amplitude of the Fourier Transform in a cardiac frequency range with an average amplitude of the Fourier Transform in a frequency range below that of the cardiac frequency.

7. The imager of claim 1 in which the stability indicators include an amplitude of the zero component of the Fourier Transform.

8. The imager of claim 1 wherein the selected one or more optical coherence images are those generated by the detector system within a sub-period of the stable time segment, the sub-period being equal to a whole number of cardiac pulse periods.

9. The imager of claim 8 wherein the whole number is 2.

10. The imager of claim 9 wherein the cardiac pulse period is determined by peak detection within a typical cardiac frequency range of the Fourier Transform.

11. The imager of claim 1 wherein the imager also includes:
    a visible light source (26) for illuminating the area of tissue surface; and
    a switching mechanism for switching illumination between the visible light source (26) and laser source (24); wherein
    the detector system (28) is further arranged to detect visible light scattered from the tissue surface and to generate output signals indicative of scattered light intensities; and
    the signal processing apparatus (30) is further arranged to form an optical image from the optical output signals and to output the optical image to the display screen (18a, 18b).

12. The imager of claim 11 wherein the visible light source (26) comprises red, green and blue light emitting diodes; the switching mechanism is arranged to switch illumination between each of the light emitting diodes and the laser source (24);
    and the signal processing apparatus (30) is arranged to form a colour optical image from each of red, green and blue output signals from the detector system (28).

13. The imager of claim 12 wherein the optical image is a video image.

14. The imager of claim 1 wherein the laser light source (24) and detector system (28) are mounted on a scan head (20), the scan head (20) being located at a distal end of two mutually hinged and pivotable arms (82, 86) and counter-balanced by a counterweight (88) that is connected by linkage rods (89, 90) to the hinged and pivotal arms (82, 86).

15. The imager of claim 1 wherein the optical coherence image is a laser speckle image.

16. The imager of claim 1 wherein the optical coherence image is a Flux image and the time-varying values extracted from the region of interest are Flux values.

17. A method of finding a stable time period during acquisition of an optical coherence image, the method comprising:
    a. Identifying a region of interest that extends spatially over an array of image pixels;
    b. Identifying one or more tested time segments, each tested time segment corresponding to different time-periods of image acquisition in which a number of successive image frames are taken;
    c. for each frame within each respective tested time segment, calculating a spatially merged value of detected signals within the region of interest;
    d. For each tested time segment, calculating the Fourier Transform of a time series of the spatially merged values to form a power spectrum and extracting one or more stability indicators therefrom;
    e. Comparing the one or more stability indicators from each tested time segment and selecting the tested time segment whose stability indicators best match pre-determined criteria; and
    f. Identifying the time period of image acquisition of the selected tested time segment as the stable time period.

18. A method of generating a representative optical coherence image, the method including the steps of finding a stable time period in accordance with claim 17 and generating the representative image from optical coherence images acquired only during the stable time period.

19. The method of claim 18 including acquiring optical images concurrently with the optical coherence images.

20. The method of claim 19 wherein the optical coherence image is a laser speckle contrast image of body tissue.

21. A method of compensating subject movement in an optical coherence image, the method including the steps of:
   a. Generating a representative optical coherence image in accordance with claim 18;
   b. Generating a reference DC image from intensity data used to generate the representative optical coherence image;
   c. Comparing a current live DC image with a previously-generated reference DC image to determine subject movement since generation of the representative image that corresponds with the reference DC image; and
   d. Moving the representative optical coherence image to compensate for subject movement.

22. A method of transferring a visible mark to an optical coherence image, the method including the steps of:
   a. Generating a representative optical coherence image in accordance with claim 18;
   b. Generating a reference DC image from intensity data used to generate the representative optical coherence image, the visible mark being detectable in the DC image;
   c. Displaying the visible mark at a corresponding position on the representative optical coherence image;
   d. Comparing a current live DC image with a previously-generated reference DC image to determine movement of the visible mark since generation of the representative image that corresponds with the reference DC image; and
   e. Moving the position at which the visible mark is displayed on the optical coherence image to display movement of the mark.

23. The method of claim 22 wherein the step of comparing a current live DC image with a previously-generated reference DC image includes the steps of identifying a relevant region in the reference DC image; cross-correlating this region with a series of successively-adjusted corresponding regions in the live DC image and finding a peak in cross-correlation values, thereby determining movement of the relevant region since generation of the reference DC image.

24. The method of claim 22 wherein the visible mark is a characteristic tip of a marker pen.

25. A method of assessing tissue viability potential including the steps of:
   a. Generating a representative optical coherence image of body tissue in accordance with claim 18;
   b. Using values generated for the representative coherence image and spatial location of regions within the tissue image, determining an indicator of tissue viability potential for each region in terms of predetermined assessment criteria that inform on the potential of the tissue to develop post-operative complications of predefined severity; and
   c. Displaying the representative image with each region displayed in a colour selected in accordance with the indicator of tissue viability potential determined for that region.

26. The imager of claim 8 wherein the cardiac pulse period is determined by peak detection within a typical cardiac frequency range of the Fourier Transform.

27. The imager of claim 11 wherein the optical image is a video image.

28. The method of claim 18 wherein the optical coherence image is a laser speckle contrast image of body tissue.

29. The method of claim 21 wherein the step of comparing a current live DC image with a previously-generated reference DC image includes the steps of identifying a relevant region in the reference DC image; cross-correlating this region with a series of successively-adjusted corresponding regions in the live DC image and finding a peak in cross-correlation values, thereby determining movement of the relevant region since generation of the reference DC image.

* * * * *